(12) United States Patent
Scheller et al.

(10) Patent No.: US 9,849,035 B2
(45) Date of Patent: *Dec. 26, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,341

(22) Filed: May 15, 2017

(65) Prior Publication Data
US 2017/0246035 A1   Aug. 31, 2017

Related U.S. Application Data

(63) Continuation of application No. 14/943,424, filed on Nov. 17, 2015, now Pat. No. 9,681,918.

(51) Int. Cl.
*A61B 18/18* (2006.01)
*A61F 9/008* (2006.01)
(Continued)

(52) U.S. Cl.
CPC ...... *A61F 9/00821* (2013.01); *A61F 9/00823* (2013.01); *A61B 18/22* (2013.01);
(Continued)

(58) Field of Classification Search
CPC .................... A61F 9/00821; A61F 9/00823
(Continued)

(56) References Cited

U.S. PATENT DOCUMENTS 3,174,851 A   3/1965 Buehler et al.
4,122,853 A   10/1978 Smith
(Continued)

FOREIGN PATENT DOCUMENTS

EP       0900547 B1   3/1999
WO   WO 2011/019581 A1   2/2001
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — William Thomson
*Assistant Examiner* — Sebastian X Lukjan
(74) *Attorney, Agent, or Firm* — Kevin P. Rollins

(57) ABSTRACT

A steerable laser probe may include a handle having a handle, a housing sleeve, a first portion of the housing sleeve having a first stiffness, a second portion of the housing sleeve having a second stiffness, an actuation control of the handle, an optic fiber disposed in an inner bore of the handle and the housing sleeve, and a shape memory wire having a pre-formed curve. An actuation of the actuation control may be configured to gradually curve the housing sleeve and the optic fiber. An actuation of the actuation control may be configured to gradually straighten the housing sleeve and the optic fiber.

20 Claims, 12 Drawing Sheets

(51) Int. Cl.
  *A61B 17/00* (2006.01)
  *A61B 18/00* (2006.01)
  *A61B 18/22* (2006.01)

(52) U.S. Cl.
  CPC .............. *A61B 2017/00318* (2013.01); *A61B 2018/00589* (2013.01); *A61B 2018/2238* (2013.01); *A61F 2009/00863* (2013.01)

(58) Field of Classification Search
  USPC ...................................................... 606/4, 16
  See application file for complete search history.

(56) References Cited

U.S. PATENT DOCUMENTS

| | | | |
|---|---|---|---|
| 4,147,443 A | 4/1979 | Skobel | |
| 4,687,293 A | 8/1987 | Randazzo | |
| 4,744,360 A | 5/1988 | Bath | |
| 4,870,952 A | 10/1989 | Martinez | |
| 5,190,050 A | 3/1993 | Nitzsche | |
| 5,228,852 A | 7/1993 | Goldsmith et al. | |
| 5,257,988 A | 11/1993 | L'Esperance, Jr. | |
| 5,322,055 A | 6/1994 | Davison et al. | |
| 5,322,064 A | 6/1994 | Lundquist | |
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,735,842 A | 4/1998 | Kruege et al. | |
| 5,855,577 A | 1/1999 | Murphy-Chutorian et al. | |
| 5,873,865 A | 2/1999 | Horzewski et al. | |
| 5,951,544 A | 9/1999 | Konwitz | |
| 6,123,699 A | 9/2000 | Webster, Jr. | |
| 6,126,654 A | 10/2000 | Giba et al. | |
| 6,178,354 B1 | 1/2001 | Gibson | |
| 6,198,974 B1 | 3/2001 | Webster, Jr. | |
| 6,330,837 B1 | 12/2001 | Charles et al. | |
| 6,352,531 B1 | 3/2002 | O'Connor et al. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,533,772 B1 | 3/2003 | Sherts et al. | |
| 6,551,302 B1 | 4/2003 | Rosinko et al. | |
| 6,554,794 B1 | 4/2003 | Mueller et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,872,214 B2 | 3/2005 | Sonnenschein et al. | |
| 6,984,230 B2 | 1/2006 | Scheller et al. | |
| 7,004,957 B1 | 2/2006 | Dampney et al. | |
| 7,226,444 B1 | 6/2007 | Ellman et al. | |
| 7,303,533 B2 | 12/2007 | Johansen et al. | |
| 7,402,158 B2 | 7/2008 | Scheller et al. | |
| 7,555,327 B2 | 6/2009 | Matlock | |
| 7,632,242 B2 | 12/2009 | Griffin et al. | |
| 7,766,904 B2 | 10/2010 | Mc Gowan, Sr. et al. | |
| 7,935,108 B2 | 5/2011 | Baxter et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,840,605 B2 | 9/2014 | Scheller et al. | |
| 8,840,607 B2 | 9/2014 | Scheller et al. | |
| 8,968,277 B2 | 1/2015 | Scheller et al. | |
| 8,951,245 B2 | 2/2015 | Scheller et al. | |
| 9,023,019 B2 | 5/2015 | Scheller et al. | |
| 9,023,020 B2 | 5/2015 | Scheller et al. | |
| 9,039,686 B2 | 5/2015 | Scheller et al. | |
| 9,089,399 B2 | 7/2015 | Scheller et al. | |
| 9,107,682 B2 | 8/2015 | Scheller et al. | |
| 9,113,995 B2 | 8/2015 | Scheller et al. | |
| 9,119,702 B2 | 9/2015 | Scheller et al. | |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0131399 A1 | 6/2005 | Loeb et al. | |
| 2005/0154379 A1 | 7/2005 | McGowen, Sr. et al. | |
| 2005/0157985 A1 | 7/2005 | McGowan, Sr. et al. | |
| 2005/0234437 A1 | 10/2005 | Baxter et al. | |
| 2005/0272975 A1 | 12/2005 | McWeeny et al. | |
| 2005/0277874 A1 | 12/2005 | Selkee | |
| 2006/0129175 A1 | 6/2006 | Griffen et al. | |
| 2006/0178674 A1 | 8/2006 | McIntyre | |
| 2006/0293270 A1 | 12/2006 | Adamis et al. | |
| 2007/0179475 A1 | 8/2007 | Scheller | |
| 2007/0185514 A1 | 8/2007 | Kirchhevel | |
| 2007/0260231 A1 | 11/2007 | Rose et al. | |
| 2008/0132761 A1 | 6/2008 | Sonnenschein et al. | |
| 2008/0208105 A1 | 8/2008 | Zelickson et al. | |
| 2008/0287938 A1 | 11/2008 | Scheller et al. | |
| 2009/0018993 A1 | 1/2009 | Dick et al. | |
| 2009/0163943 A1 | 6/2009 | Cavanaugh et al. | |
| 2009/0187170 A1 | 7/2009 | Auld et al. | |
| 2009/0312750 A1 | 12/2009 | Spaide | |
| 2010/0004642 A1* | 1/2010 | Lumpkin | A61B 18/22 606/4 |
| 2010/0191224 A1 | 7/2010 | Butcher | |
| 2010/0268234 A1 | 10/2010 | Aho et al. | |
| 2010/0331883 A1 | 12/2010 | Schmitz et al. | |
| 2011/0028947 A1 | 2/2011 | Scheller et al. | |
| 2011/0144627 A1 | 6/2011 | Smith | |
| 2011/0144630 A1* | 6/2011 | Loeb | A61B 18/22 606/16 |
| 2011/0280653 A1 | 11/2011 | Sjostedt et al. | |
| 2012/0116361 A1 | 5/2012 | Hanlon et al. | |
| 2012/0245569 A1 | 9/2012 | Papac et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0090635 A1 | 4/2013 | Mansour | |
| 2013/0096541 A1 | 4/2013 | Scheller et al. | |
| 2013/0116671 A1 | 5/2013 | Scheller et al. | |
| 2013/0144278 A1 | 6/2013 | Papac et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |
| 2013/0281994 A1 | 10/2013 | Scheller et al. | |
| 2013/0304043 A1 | 11/2013 | Scheller et al. | |
| 2013/0304048 A1 | 11/2013 | Scheller et al. | |
| 2014/0005642 A1 | 1/2014 | Scheller et al. | |
| 2014/0039471 A1 | 2/2014 | Scheller et al. | |
| 2014/0039472 A1 | 2/2014 | Scheller et al. | |
| 2014/0039475 A1 | 2/2014 | Scheller et al. | |
| 2014/0046307 A1 | 2/2014 | Scheller et al. | |
| 2014/0052115 A1 | 2/2014 | Zeid et al. | |
| 2014/0066907 A1 | 3/2014 | Scheller et al. | |
| 2014/0066912 A1 | 3/2014 | Scheller et al. | |
| 2014/0074073 A1 | 3/2014 | Scheller et al. | |
| 2014/0074079 A1 | 3/2014 | Scheller et al. | |
| 2014/0088572 A1 | 3/2014 | Scheller et al. | |
| 2014/0088576 A1 | 3/2014 | Scheller et al. | |
| 2014/0107628 A1 | 4/2014 | Scheller et al. | |
| 2014/0107629 A1 | 4/2014 | Scheller et al. | |
| 2015/0038950 A1 | 2/2015 | Scheller et al. | |

FOREIGN PATENT DOCUMENTS

| WO | WO 2006/091597 A1 | 8/2006 |
|---|---|---|
| WO | WO 2007/038433 A2 | 4/2007 |
| WO | WO 2013/133717 | 9/2013 |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

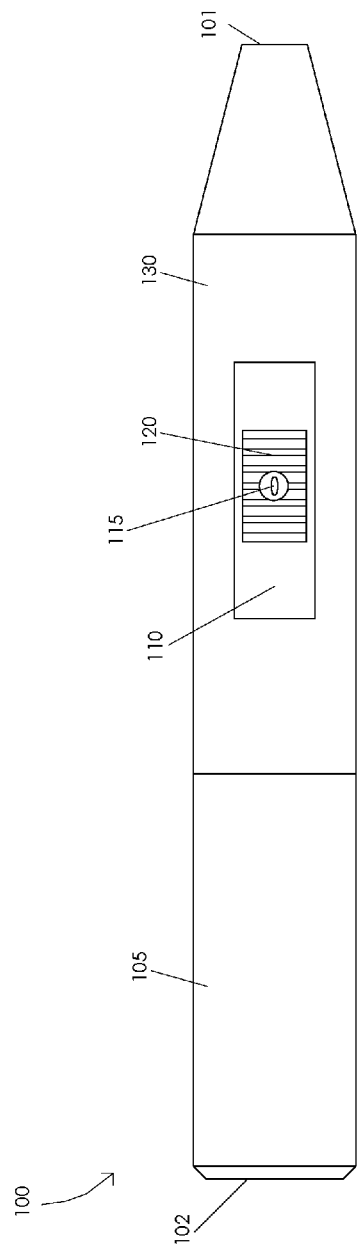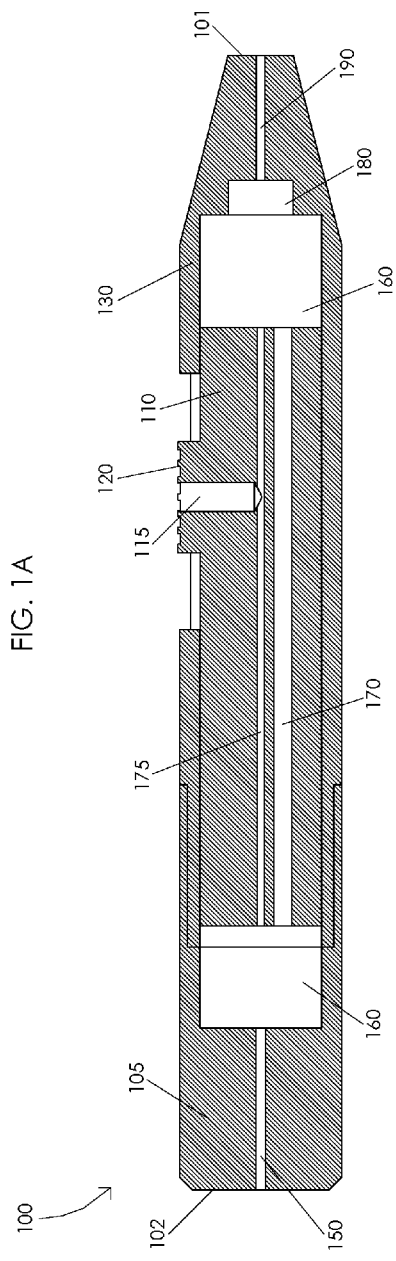

US 9,849,035 B2

STEERABLE LASER PROBE

CROSS-REFERENCE TO RELATED APPLICATIONS

This application is a continuation of prior application Ser. No. 14/943,424 filed Nov. 17, 2015.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. Illustratively, a steerable laser probe may comprise a handle having a handle distal end and a handle proximal end, a housing sleeve having a housing sleeve distal end and a housing sleeve proximal end, a first portion of the housing sleeve having a first stiffness, a second portion of the housing sleeve having a second stiffness, an actuation control of the handle, an optic fiber disposed in an inner bore of the handle and the housing sleeve, and a shape memory wire having a pre-formed curve. In one or more embodiments, an actuation of the actuation control may be configured to gradually curve the housing sleeve and the optic fiber. Illustratively, an actuation of the actuation control may be configured to gradually straighten the housing sleeve and the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

DETAILED DESCRIPTION OF AN ILLUSTRATIVE EMBODIMENT

Figure 2:
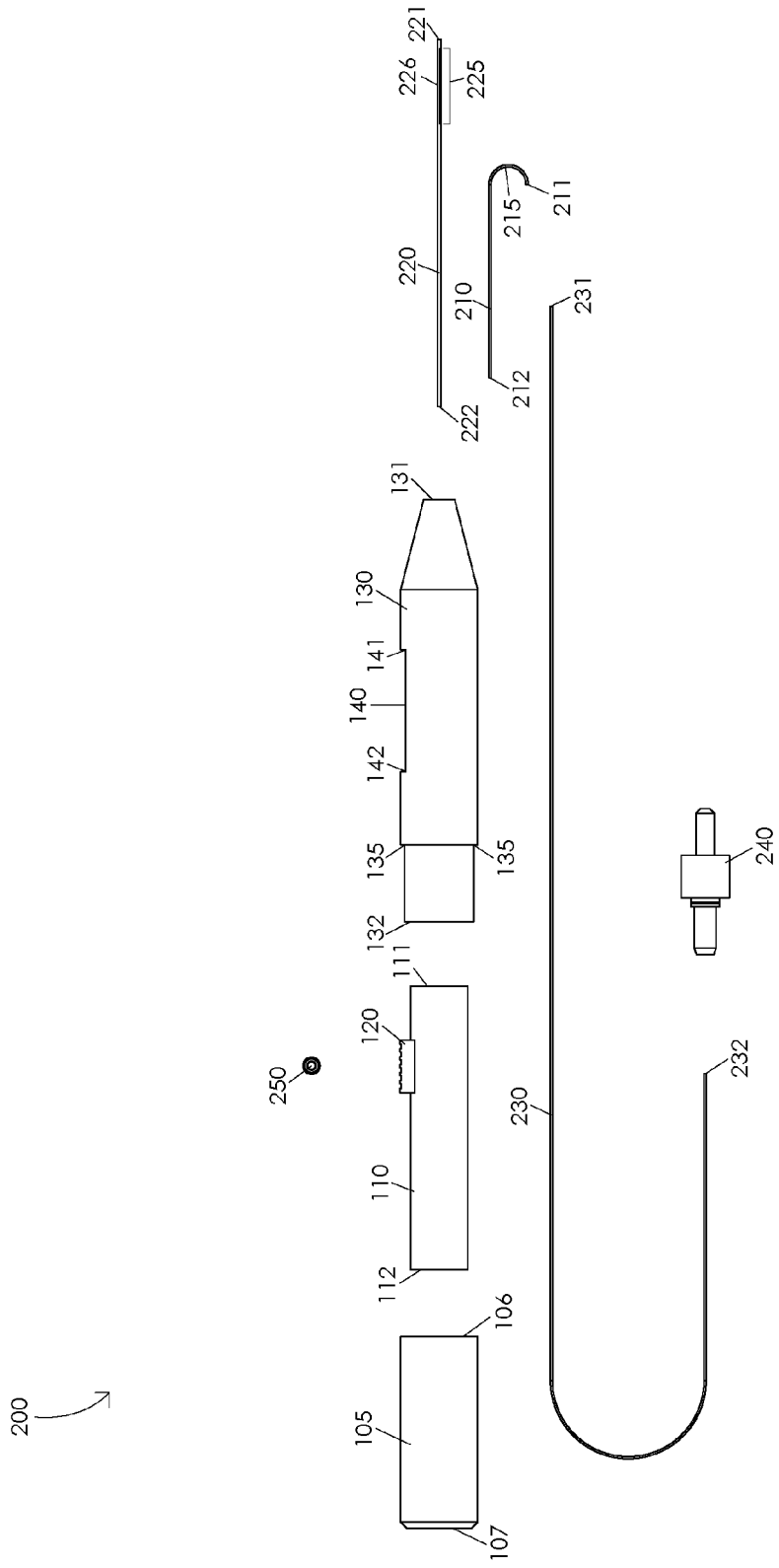
FIG. 2 is a schematic diagram illustrating an exploded view of a steerable laser probe assembly.

FIGS. 1A and 1B are schematic diagrams illustrating a handle 100. FIG. 1A illustrates a top view of handle 100. Illustratively, handle 100 may comprise a handle distal end 101 and a handle proximal end 102. In one or more embodiments, handle 100 may comprise a handle end cap 105 having a handle end cap distal end 106 and a handle end cap proximal end 107, an actuation mechanism 110 having an actuation mechanism distal end 111 and an actuation mechanism proximal end 112, a fixation mechanism housing 115, an actuation control 120, a handle base 130 having a handle base distal end 131 and a handle base proximal end 132, and an actuation control guide 140 having an actuation control guide distal end 141 and an actuation control guide proximal end 142. Illustratively, handle 100 may be manufactured from any suitable material, e.g., polymers, metals, metal alloys, etc., or from any combination of suitable materials.

FIG. 1B illustrates a cross-sectional view of handle 100. Illustratively, handle 100 may comprise an optic fiber guide 150, an actuation mechanism guide 160, an inner bore 170, a shape memory wire housing 175, a pressure mechanism housing 180, and a housing sleeve housing 190. Handle end cap 105, actuation mechanism 110, actuation control 120, and handle base 130 may be manufactured from any suitable material, e.g., polymers, metals, metal alloys, etc., or from any combination of suitable materials.

Illustratively, actuation mechanism 110 may be disposed within handle end cap 105 and handle base 130. In one or more embodiments, actuation mechanism 110 may be configured to actuate within handle end cap 105 and handle base 130, e.g., actuation mechanism 110 may be configured to actuate within actuation mechanism guide 160. Illustratively, a portion of actuation mechanism guide 160 may be configured to facilitate an actuation of actuation mechanism 110 within actuation mechanism guide 160. In one or more embodiments, a portion of actuation mechanism guide 160 may comprise a lubricant, e.g., Teflon, configured to facilitate an actuation of actuation mechanism 110 within actuation mechanism guide 160. Illustratively, actuation control 120 may be disposed within actuation control guide 140, e.g., actuation control 120 may be configured to actuate within actuation control guide 140. In one or more embodiments, an actuation of actuation control 120 within actuation control guide 140 may be configured to actuate actuation mechanism 110 within actuation mechanism guide 160.

Illustratively, an actuation of actuation control 120 within actuation control guide 140, e.g., towards actuation control guide distal end 141 and away from actuation control guide proximal end 142, may be configured to actuate actuation mechanism 110 within actuation mechanism guide 160, e.g., towards handle distal end 101 and away from handle proximal end 102. In one or more embodiments, an actuation of actuation mechanism 110 towards handle distal end 101 and away from handle proximal end 102 may be configured to extend shape memory wire housing 175 relative to housing sleeve housing 190. Illustratively, an actuation of actuation control 120 within actuation control guide 140, e.g., towards actuation control guide proximal end 142 and away from actuation control guide distal end 141, may be configured to actuate actuation mechanism 110 within actuation mechanism guide 160, e.g., towards handle proximal end 102 and away from handle distal end 101. In one or more embodiments, an actuation of actuation mechanism 110 towards handle proximal end 102 and away from handle distal end 101 may be configured to retract shape memory wire housing 175 relative to housing sleeve housing 190.

FIG. 2 is a schematic diagram illustrating an exploded view of a steerable laser probe assembly 200. Illustratively, a steerable laser probe assembly 200 may comprise a handle end cap 105 having a handle end cap distal end 106 and a handle end cap proxies mal end 107; an actuation mechanism 110 having an actuation mechanism distal end 111 and an actuation mechanism proximal end 112; an actuation control 120; a handle base 130 having a handle base distal end 131 and a handle base proximal end 132; a shape memory wire 210 having a shape memory wire distal end 211, a shape memory wire proximal end 212, and a pre-formed curve 215; a housing sleeve 220 having a housing sleeve distal end 221, a housing sleeve proximal end 222, a first housing sleeve portion 225, and a second housing sleeve portion 226; an optic fiber 230 having an optic fiber distal end 231 and an optic fiber proximal end 232; a light source interface 240; and a fixation mechanism 250. In one or more embodiments, light source interface 240 may be configured to interface with optic fiber 230, e.g., at optic fiber proximal end 232. Illustratively, light source interface 240 may comprise a standard light source connecter, e.g., an SMA connector.

In one or more embodiments, housing sleeve 220 may be manufactured with dimensions configured for microsurgical procedures. Housing sleeve 220 may be manufactured from any suitable material, e.g., polymers, metals, metal alloys, etc., or from any combination of suitable materials. In one or more embodiments, first housing sleeve portion 225 may have a first stiffness. Illustratively, second housing sleeve portion 226 may have a second stiffness. In one or more embodiments, the second stiffness may be greater than the first stiffness. Illustratively, first housing sleeve portion 225 may comprise a first material having a first stiffness. In one or more embodiments, second housing sleeve portion 226 may comprise a second material having a second stiffness. Illustratively, the second stiffness may be greater than the first stiffness.

In one or more embodiments, housing sleeve 220 may comprise a non-uniform inner diameter or a non-uniform outer diameter, e.g., to vary a stiffness of one or more portions of housing sleeve 220. Illustratively, a first housing sleeve portion 225 may comprise a first inner diameter of housing sleeve 220 and a second housing sleeve portion 226 may comprise a second inner diameter of housing sleeve 220. In one or more embodiments, the first inner diameter of housing sleeve 220 may be larger than the second inner diameter of housing sleeve 220. Illustratively, a first housing sleeve portion 225 may comprise a first outer diameter of housing sleeve 220 and a second housing sleeve portion 226 may comprise a second outer diameter of housing sleeve 220. In one or more embodiments, the first outer diameter of housing sleeve 220 may be smaller than the second outer diameter of housing sleeve 220.

In one or more embodiments, first housing sleeve portion 225 may comprise one or more apertures configured to produce a first stiffness of first housing sleeve portion 225. Illustratively, second housing sleeve portion 226 may comprise a solid portion of housing sleeve 220 having a second stiffness. In one or more embodiments, the second stiffness may be greater than the first stiffness. Illustratively, first housing sleeve portion 225 may comprise one or more apertures configured to produce a first stiffness of first housing sleeve portion 225. In one or more embodiments, second housing sleeve portion 226 may comprise one or more apertures configured to produce a second stiffness of second housing sleeve portion 226. Illustratively, the second stiffness may be greater than the first stiffness.

In one or more embodiments, first housing sleeve portion 225 may comprise a plurality of slits configured to separate one or more solid portions of housing sleeve 220. Illustratively, a plurality of slits may be cut, e.g., laser cut, into first housing sleeve portion 225. In one or more embodiments, first housing sleeve portion 225 may comprise a plurality of slits configured to minimize a force of friction between housing sleeve 220 and a cannula, e.g., as housing sleeve 220 is inserted into the cannula or as housing sleeve 220 is extracted from the cannula. For example, each slit of the plurality of slits may comprise one or more arches configured to minimize a force of friction between housing sleeve 220 and a cannula.

Illustratively, a portion of housing sleeve 220 may be fixed to a portion of handle base 130, e.g., housing sleeve proximal end 222 may be fixed to handle base distal end 131. In one or more embodiments, a portion of housing sleeve 220 may be fixed to a portion of handle base 130, e.g., by an adhesive or any suitable fixation means. Illustratively, a portion of housing sleeve 220 may be fixed to a portion of handle 100, e.g., housing sleeve proximal end 222 may be fixed to handle distal end 101. In one or more embodiments, a portion of housing sleeve 220 may be fixed to a portion of handle 100, e.g., by an adhesive or any suitable fixation means. Illustratively, a portion of housing sleeve 220 may be disposed within housing sleeve housing 190, e.g., housing sleeve proximal end 222 may be disposed within housing sleeve housing 190. In one or more embodiments, a portion of housing sleeve 220 may be fixed within housing sleeve housing 190, e.g., by an adhesive or any suitable fixation means. For example, a portion of housing sleeve 220 may be fixed within housing sleeve housing 190 by a press fit, a setscrew, etc.

Illustratively, optic fiber 230 may be configured to transmit light, e.g., optic fiber 230 may be configured to transmit laser light, illumination light, etc. In one or more embodiments, optic fiber 230 may be disposed in optic fiber guide 150, actuation mechanism guide 160, inner bore 170, housing sleeve housing 190, and housing sleeve 220. Illustratively, optic fiber 230 may be disposed within housing sleeve 220 wherein optic fiber distal end 231 may be adjacent to housing sleeve distal end 221. In one or more embodiments, optic fiber 230 may be disposed within housing sleeve 220 wherein a portion of optic fiber 230 may be adjacent to a portion of second housing sleeve portion 226. Illustratively, a portion of optic fiber 230 may be fixed to a portion of housing sleeve 220, e.g., by an adhesive or any suitable fixation means.

In one or more embodiments, at least a portion of shape memory wire 210 may comprise a shape memory material, e.g., Nitinol. Illustratively, shape memory wire 210 may comprise a pre-formed curve 215. In one or more embodiments, pre-formed curve 215 may comprise a shape memory material, e.g., Nitinol. In one or more embodiments, shape memory wire 210 may be disposed in shape memory wire housing 175, actuation mechanism guide 160, housing sleeve housing 190, and housing sleeve 220. Illustratively, shape memory wire distal end 211 may be disposed within housing sleeve 220. In one or more embodiments, at least a portion of pre-formed curve 215 may be disposed within housing sleeve 220. Illustratively, shape memory wire proximal end 212 may be disposed within shape memory wire housing 175. In one or more embodiments, a portion of shape memory wire 210 may be fixed within shape memory wire housing 175, e.g., by an adhesive or any suitable fixation means. Illustratively, fixation mechanism 250 may be configured to fix a portion of shape memory wire 210 to actuation mechanism 110. In one or more embodiments, fixation mechanism 250 may be disposed within fixation mechanism housing 115. Illustratively, a portion of fixation mechanism 250 may be disposed in shape memory wire housing 175. In one or more embodiments, fixation mechanism 250 may comprise a setscrew configured to fix shape memory wire 210 in a position relative to actuation mechanism 110. Illustratively, shape memory wire 210 may be fixed within shape memory wire housing 175, e.g., by a press fit or any suitable fixation means.

In one or more embodiments, an actuation of actuation control 120 within actuation control guide 140, e.g., towards actuation control guide distal end 141 and away from actuation control guide proximal end 142, may be configured to actuate actuation mechanism 110 within actuation mechanism guide 160, e.g., towards handle distal end 101 and away from handle proximal end 102. Illustratively, an actuation of actuation mechanism 110 towards handle distal end 101 and away from handle proximal end 102 may be configured to extend shape memory wire housing 175 relative to housing sleeve housing 190. In one or more embodiments, an extension of shape memory wire housing 175 relative to housing sleeve housing 190 may be configured to extend shape memory wire 210 relative to housing sleeve 220. Illustratively, an extension of shape memory wire 210 relative to housing sleeve 220 may be configured to extend pre-formed curve 215 within housing sleeve 220, e.g., towards housing sleeve distal end 221 and away from housing sleeve proximal end 222. In one or more embodiments, an extension of pre-formed curve 215 towards housing sleeve distal end 221 and away from housing sleeve proximal end 222 may be configured to extend a portion of pre-formed curve 215 over a portion of first housing sleeve portion 225. Illustratively, a portion of housing sleeve 220 may be configured to generally straighten pre-formed curve 215. In one or more embodiments, an extension of pre-formed curve 215 over a portion of first housing sleeve portion 225 may be configured to cause a generally straightened pre-formed curve 215 to gradually curve. Illustratively, a stiffness of first housing sleeve portion 225 may be configured to allow pre-formed curve 215 to gradually curve. In one or more embodiments, a gradual curving of shape memory wire 210 within housing sleeve 220 may be configured to gradually curve housing sleeve 220. Illustratively, a gradual curving of housing sleeve 220 may be configured to gradually curve optic fiber 230. In one or more embodiments, an actuation of actuation control 120 within actuation control guide 140, e.g., towards actuation control guide distal end 141 and away from actuation control guide proximal end 142, may be configured to gradually curve optic fiber 230. Illustratively, an extension of actuation control 120 relative to actuation control guide proximal end 142 may be configured to gradually curve optic fiber 230.

In one or more embodiments, an actuation of actuation control 120 within actuation control guide 140, e.g., towards actuation control guide proximal end 142 and away from actuation control guide distal end 141, may be configured to actuate actuation mechanism 110 within actuation mechanism guide 160, e.g., towards handle proximal end 102 and away from handle distal end 101. Illustratively, an actuation of actuation mechanism 110 towards handle proximal end 102 and away from handle distal end 101 may be configured to retract shape memory wire housing 175 relative to housing sleeve housing 190. In one or more embodiments, a retraction of shape memory wire housing 175 relative to housing sleeve housing 190 may be configured to retract shape memory wire 210 relative to housing sleeve 220. Illustratively, a retraction of shape memory wire 210 relative to housing sleeve 220 may be configured to retract pre-formed curve 215 within housing sleeve 220, e.g., towards housing sleeve proximal end 222 and away from housing sleeve distal end 221. In one or more embodiments, a retraction of pre-formed curve 215 towards housing sleeve proximal end 222 and away from housing sleeve distal end 221 may be configured to retract a portion of pre-formed curve 215 away from a portion of first housing sleeve portion 225. Illustratively, a portion of housing sleeve 220 may be configured to generally straighten pre-formed curve 215. In one or more embodiments, a retraction of pre-formed curve 215 away from a portion of first housing sleeve portion 225 may be configured to cause pre-formed curve 215 to gradually straighten. Illustratively, a stiffness of housing sleeve 220 may be configured to gradually straighten pre-formed curve 215. In one or more embodiments, a gradual straightening of shape memory wire 210 within housing sleeve 220 may be configured to gradually straighten housing sleeve 220. Illustratively, a gradual straightening of housing sleeve 220 may be configured to gradually straighten optic fiber 230. In one or more embodiments, an actuation of actuation control 120 within actuation control guide 140, e.g., towards actuation control guide proximal end 142 and away from actuation control guide distal end 141, may be configured to gradually straighten optic fiber 230. Illustratively, a retraction of actuation control 120 relative to actuation control guide proximal end 142 may be configured to gradually straighten optic fiber 230.

Figure 3A:
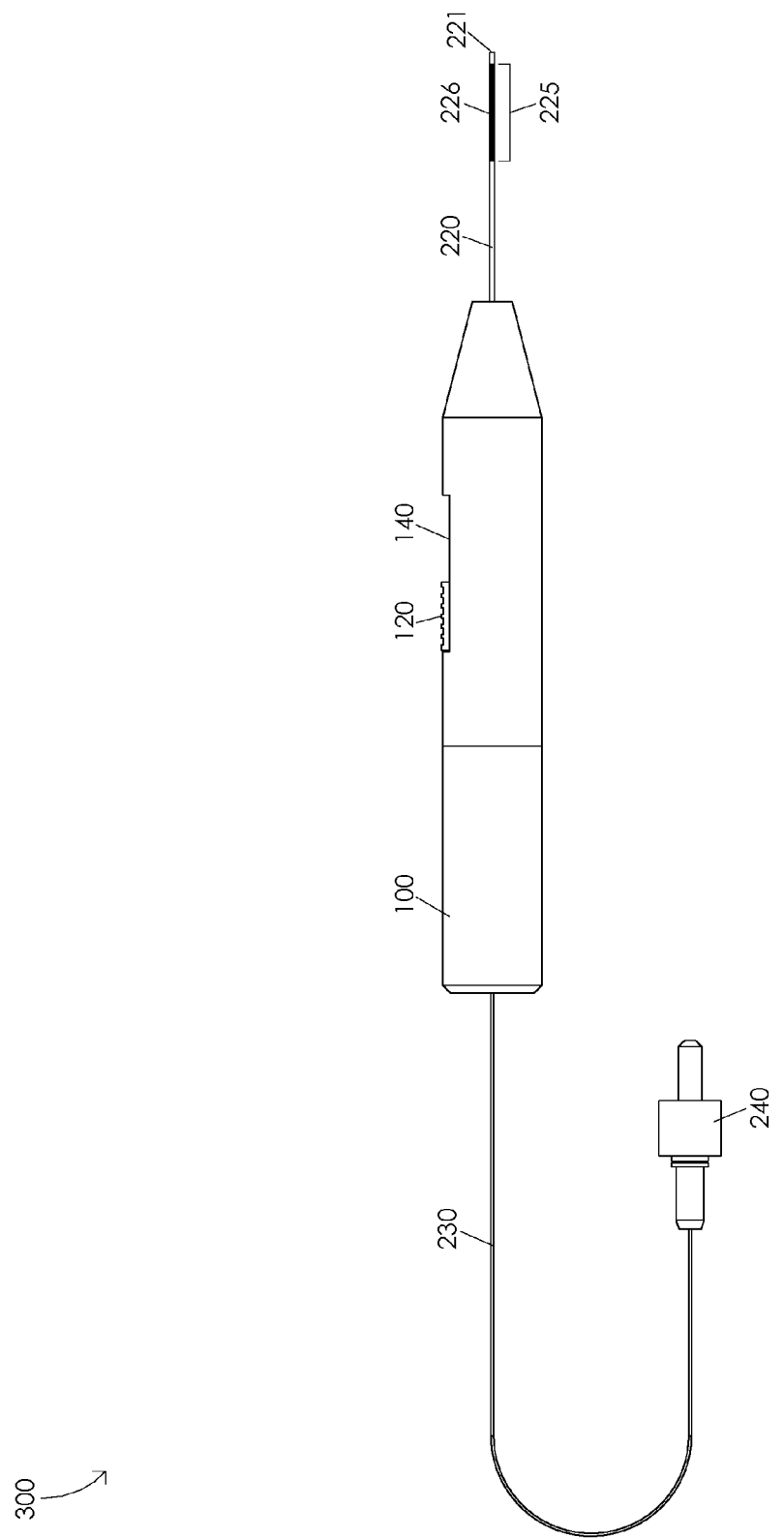
FIGS. 3A, 3B, 3C, 3D, and 3E are schematic diagrams illustrating a gradual curving of an optic fiber.

FIGS. 3A, 3B, 3C, 3D, and 3E are schematic diagrams illustrating a gradual curving of an optic fiber 230. FIG. 3A illustrates a straight optic fiber 300. In one or more embodiments, optic fiber 230 may comprise a straight optic fiber 300, e.g., when actuation control 120 is fully retracted relative to actuation control guide proximal end 142. Illustratively, optic fiber 230 may comprise a straight optic fiber 300, e.g., when actuation mechanism 110 is fully retracted relative to handle proximal end 102. In one or more embodiments, optic fiber 230 may comprise a straight optic fiber 300, e.g., when shape memory wire 210 is fully retracted relative to housing sleeve 220. Illustratively, optic fiber 230 may comprise a straight optic fiber 300, e.g., when pre-formed curve 215 is fully retracted relative to first housing sleeve portion 225. In one or more embodiments, optic fiber 230 may comprise a straight optic fiber 300, e.g., when pre-formed curve 215 is generally straightened by a portion of housing sleeve 220. Illustratively, a line tangent to optic fiber distal end 231 may be parallel to a line tangent to housing sleeve proximal end 222, e.g., when optic fiber 230 comprises a straight optic fiber 300.

Figure 3B:
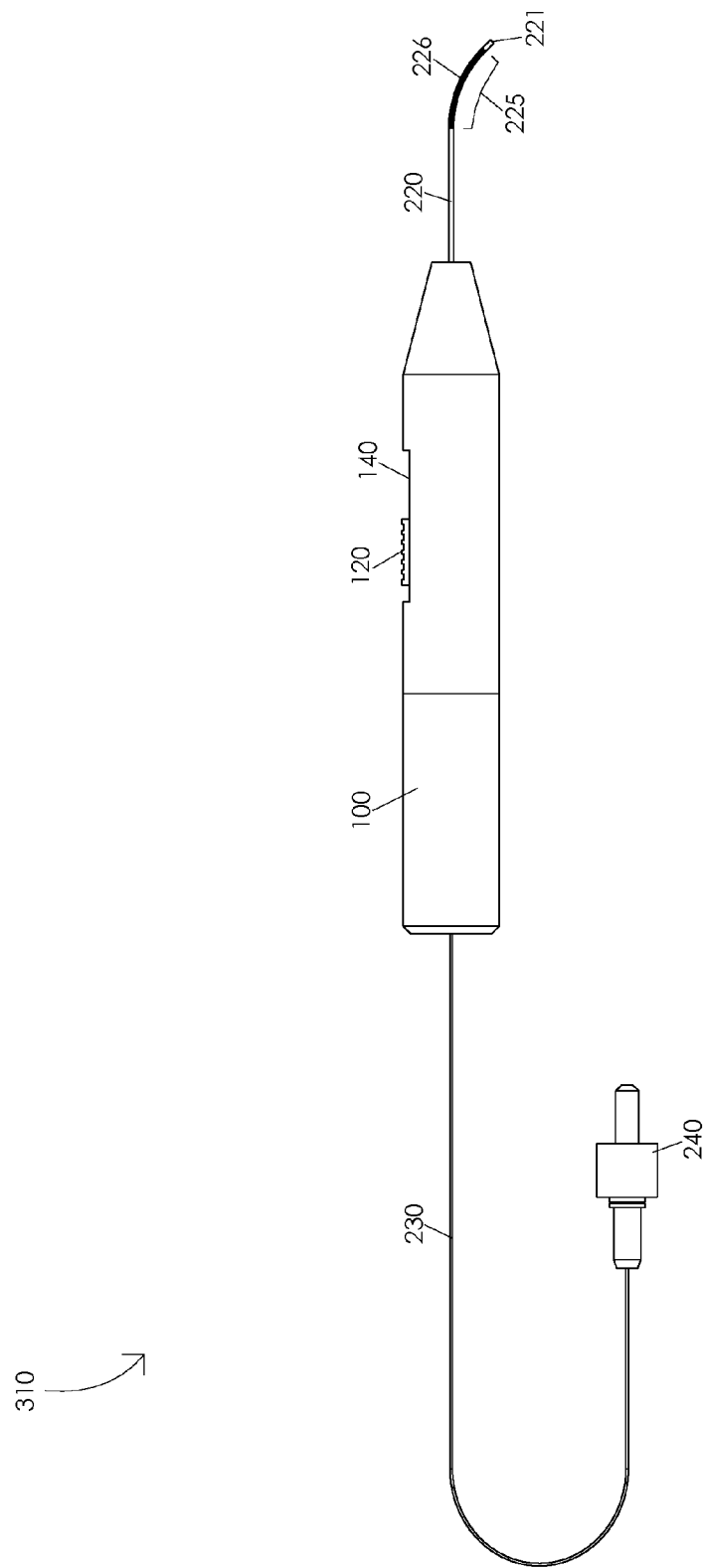

FIG. 3B illustrates an optic fiber in a first curved position 310. In one or more embodiments, an actuation of actuation control 120 within actuation control guide 140, e.g., towards actuation control guide distal end 141 and away from actuation control guide proximal end 142, may be configured to gradually curve optic fiber 230 from a straight optic fiber 300 to an optic fiber in a first curved position 310. Illustratively, an actuation of actuation control 120 towards actuation control guide distal end 141 and away from actuation control guide proximal end 142 may be configured to extend actuation mechanism 110 within actuation mechanism guide 160, e.g., towards handle distal end 101 and away from handle proximal end 102. In one or more embodiments, an extension of actuation mechanism 110 within actuation mechanism guide 160 may be configured to extend shape memory wire 210 relative to housing sleeve 220. Illustratively, an extension of shape memory wire 210 relative to housing sleeve 220 may be configured to extend pre-formed curve 215 within housing sleeve 220, e.g., towards housing sleeve distal end 221 and away from housing sleeve proximal end 222. In one or more embodiments, an extension of pre-formed curve 215 within housing sleeve 220 may be configured to extend a portion of pre-formed curve 215 over first housing sleeve portion 225. Illustratively, an extension of a portion of pre-formed curve 215 over first housing sleeve portion 225 may be configured to gradually curve housing sleeve 220. In one or more embodiments, a gradual curving of housing sleeve 220 may be configured to gradually curve optic fiber 230, e.g., from a straight optic fiber 300 to an optic fiber in a first curved position 310. Illustratively, a line tangent to optic fiber distal end 231 may intersect a line tangent to housing sleeve proximal end 222 at a first angle, e.g., when optic fiber 230 comprises an optic fiber in a first curved position 310. In one or more embodiments, the first angle may comprise any angle greater than zero degrees. For example, the first angle may comprise a 45 degree angle.

Figure 3C:
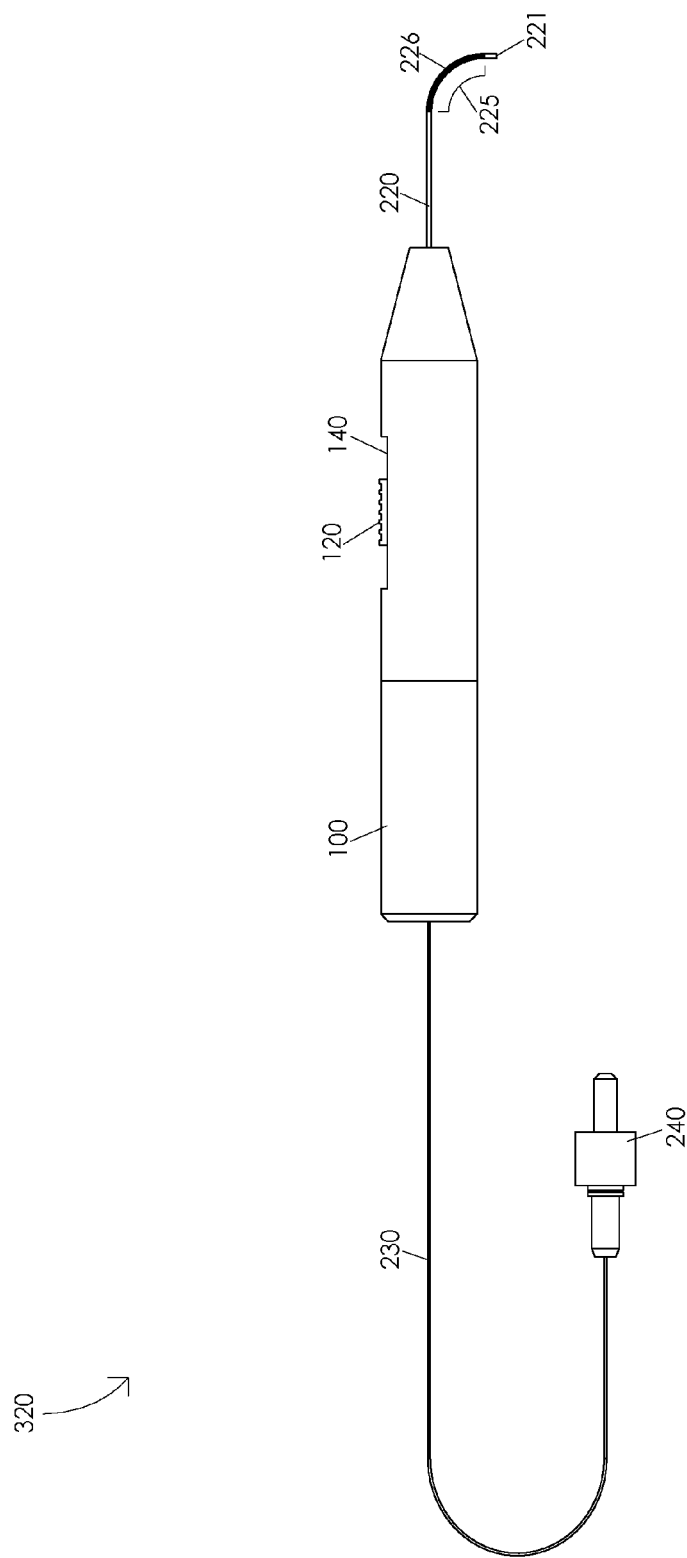

FIG. 3C illustrates an optic fiber in a second curved position 320. In one or more embodiments, an actuation of actuation control 120 within actuation control guide 140, e.g., towards actuation control guide distal end 141 and away from actuation control guide proximal end 142, may be configured to gradually curve optic fiber 230 from an optic fiber in a first curved position 310 to an optic fiber in a second curved position 320. Illustratively, an actuation of actuation control 120 towards actuation control guide distal end 141 and away from actuation control guide proximal end 142 may be configured to extend actuation mechanism 110 within actuation mechanism guide 160, e.g., towards handle distal end 101 and away from handle proximal end 102. In one or more embodiments, an extension of actuation mechanism 110 within actuation mechanism guide 160 may be configured to extend shape memory wire 210 relative to housing sleeve 220. Illustratively, an extension of shape memory wire 210 relative to housing sleeve 220 may be configured to extend pre-formed curve 215 within housing sleeve 220, e.g., towards housing sleeve distal end 221 and away from housing sleeve proximal end 222. In one or more embodiments, an extension of pre-formed curve 215 within housing sleeve 220 may be configured to extend a portion of pre-formed curve 215 over first housing sleeve portion 225. Illustratively, an extension of a portion of pre-formed curve 215 over first housing sleeve portion 225 may be configured to gradually curve housing sleeve 220. In one or more embodiments, a gradual curving of housing sleeve 220 may be configured to gradually curve optic fiber 230, e.g., from an optic fiber in a first curved position 310 to an optic fiber in a second curved position 320. Illustratively, a line tangent to optic fiber distal end 231 may intersect a line tangent to housing sleeve proximal end 222 at a second angle, e.g., when optic fiber 230 comprises an optic fiber in a second curved position 320. In one or more embodiments, the second angle may comprise any angle greater than the first angle. For example, the second angle may comprise a 90 degree angle.

Figure 3D:
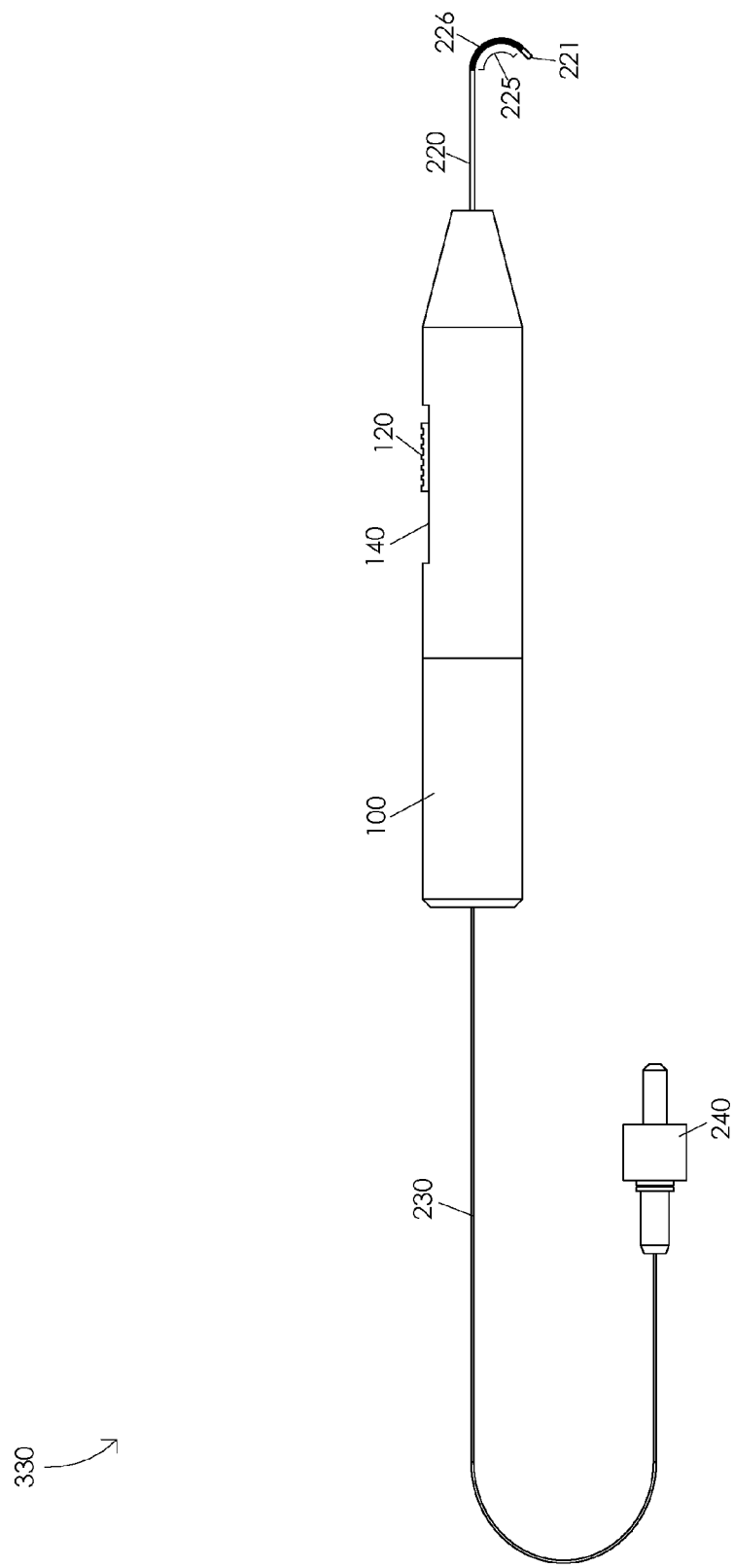

FIG. 3D illustrates an optic fiber in a third curved position 330. In one or more embodiments, an actuation of actuation control 120 within actuation control guide 140, e.g., towards actuation control guide distal end 141 and away from actuation control guide proximal end 142, may be configured to gradually curve optic fiber 230 from an optic fiber in a second curved position 320 to an optic fiber in a third curved position 330. Illustratively, an actuation of actuation control 120 towards actuation control guide distal end 141 and away from actuation control guide proximal end 142 may be configured to extend actuation mechanism 110 within actuation mechanism guide 160, e.g., towards handle distal end 101 and away from handle proximal end 102. In one or more embodiments, an extension of actuation mechanism 110 within actuation mechanism guide 160 may be configured to extend shape memory wire 210 relative to housing sleeve 220. Illustratively, an extension of shape memory wire 210 relative to housing sleeve 220 may be configured to extend pre-formed curve 215 within housing sleeve 220, e.g., towards housing sleeve distal end 221 and away from housing sleeve proximal end 222. In one or more embodiments, an extension of pre-formed curve 215 within housing sleeve 220 may be configured to extend a portion of pre-formed curve 215 over first housing sleeve portion 225. Illustratively, an extension of a portion of pre-formed curve 215 over first housing sleeve portion 225 may be configured to gradually curve housing sleeve 220. In one or more embodiments, a gradual curving of housing sleeve 220 may be configured to gradually curve optic fiber 230, e.g., from an optic fiber in a second curved position 320 to an optic fiber in a third curved position 330. Illustratively, a line tangent to optic fiber distal end 231 may intersect a line tangent to housing sleeve proximal end 222 at a third angle, e.g., when optic fiber 230 comprises an optic fiber in a third curved position 330. In one or more embodiments, the third angle may comprise any angle greater than the second angle. For example, the third angle may comprise a 135 degree angle.

Figure 3E:
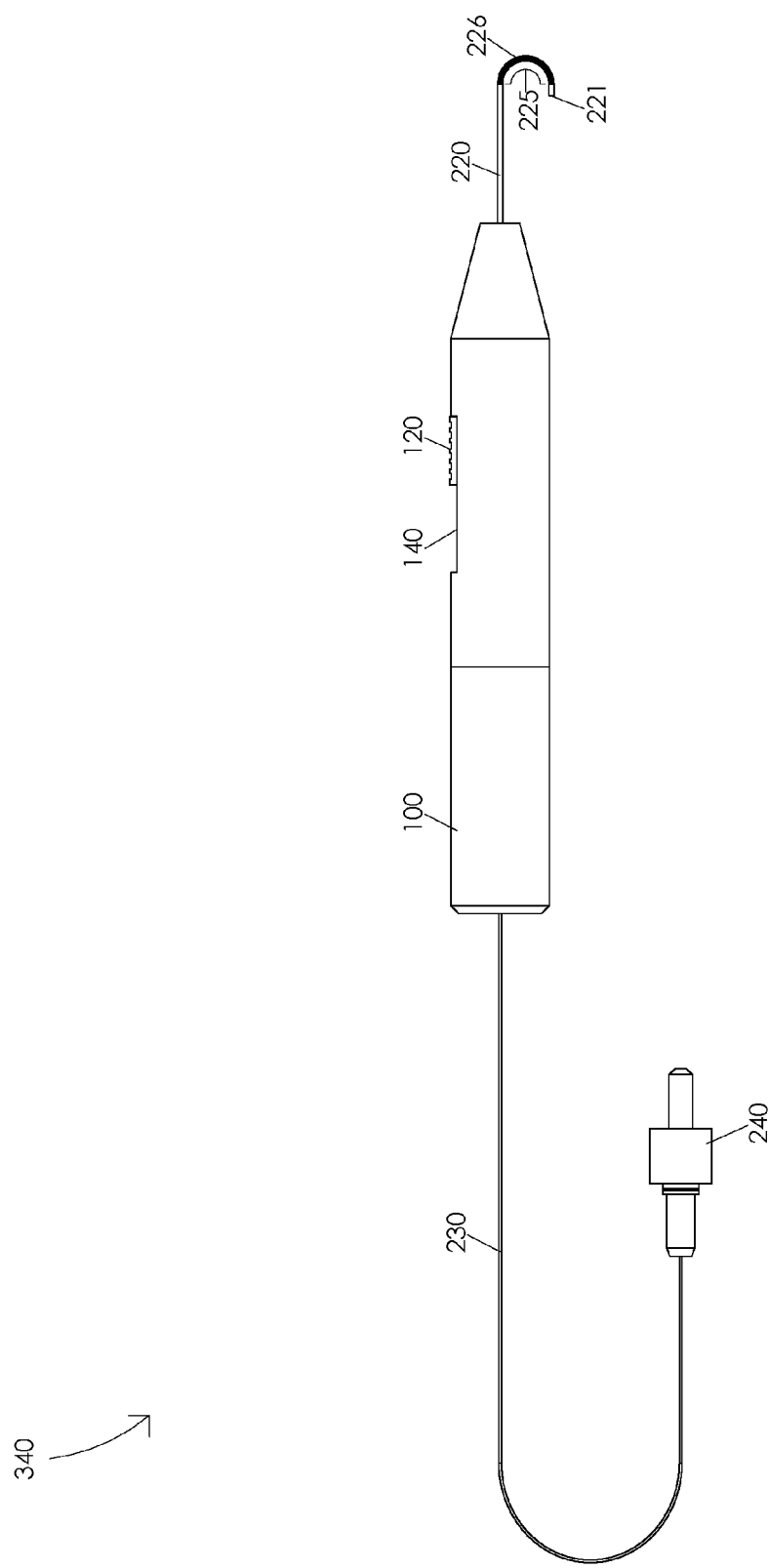

FIG. 3E illustrates an optic fiber in a fourth curved position 340. In one or more embodiments, an actuation of actuation control 120 within actuation control guide 140, e.g., towards actuation control guide distal end 141 and away from actuation control guide proximal end 142, may be configured to gradually curve optic fiber 230 from an optic fiber in a second curved position 320 to an optic fiber in a third curved position 330. Illustratively, an actuation of actuation control 120 towards actuation control guide distal end 141 and away from actuation control guide proximal end 142 may be configured to extend actuation mechanism 110 within actuation mechanism guide 160, e.g., towards handle distal end 101 and away from handle proximal end 102. In one or more embodiments, an extension of actuation mechanism 110 within actuation mechanism guide 160 may be configured to extend shape memory wire 210 relative to housing sleeve 220. Illustratively, an extension of shape memory wire 210 relative to housing sleeve 220 may be configured to extend pre-formed curve 215 within housing sleeve 220, e.g., towards housing sleeve distal end 221 and away from housing sleeve proximal end 222. In one or more embodiments, an extension of pre-formed curve 215 within housing sleeve 220 may be configured to extend a portion of pre-formed curve 215 over first housing sleeve portion 225. Illustratively, an extension of a portion of pre-formed curve 215 over first housing sleeve portion 225 may be configured to gradually curve housing sleeve 220. In one or more embodiments, a gradual curving of housing sleeve 220 may be configured to gradually curve optic fiber 230, e.g., from an optic fiber in a third curved position 330 to an optic fiber in a fourth curved position 340. Illustratively, a line tangent to optic fiber distal end 231 may be parallel to a line tangent to housing sleeve proximal end 222, e.g., when optic fiber 230 comprises an optic fiber in a fourth curved position 340.

In one or more embodiments, one or more properties of a steerable laser probe may be adjusted to attain one or more desired steerable laser probe features. Illustratively, a length that housing sleeve distal end 221 extends from handle distal end 101 may be adjusted to vary an amount of actuation of actuation control 120 configured to curve housing sleeve 220 to a particular curved position. In one or more embodiments, a stiffness of first housing sleeve portion 225 or a stiffness of second housing sleeve portion 226 may be adjusted to vary an amount of actuation of actuation control 120 configured to curve housing sleeve 220 to a particular curved position. Illustratively, a material comprising first housing sleeve portion 225 or a material comprising second housing sleeve portion 226 may be adjusted to vary an amount of actuation of actuation control 120 configured to curve housing sleeve 220 to a particular curved position.

In one or more embodiments, a number of apertures in housing sleeve 220 may be adjusted to vary an amount of actuation of actuation control 120 configured to curve housing sleeve 220 to a particular curved position. Illustratively, a location of one or more apertures in housing sleeve 220 may be adjusted to vary an amount of actuation of actuation control 120 configured to curve housing sleeve 220 to a particular curved position. In one or more embodiments, a geometry of one or more apertures in housing sleeve 220 may be adjusted to vary an amount of actuation of actuation control 120 configured to curve housing sleeve 220 to a particular curved position. Illustratively, a geometry of one or more apertures in housing sleeve 220 may be uniform, e.g., each aperture of the one or more apertures may have a same geometry. In one or more embodiments, a geometry of one or more apertures in housing sleeve 220 may be non-uniform, e.g., a first aperture in housing sleeve 220 may have a first geometry and a second aperture in housing sleeve 220 may have a second geometry.

Illustratively, a stiffness of first housing sleeve portion 225 or a stiffness of second housing sleeve portion 226 may be adjusted to vary a bend radius of housing sleeve 220. In one or more embodiments, a stiffness of first housing sleeve portion 225 or a stiffness of second housing sleeve portion 226 may be adjusted to vary a radius of curvature of housing sleeve 220, e.g., when housing sleeve 220 is in a particular curved position. Illustratively, a number of apertures in housing sleeve 220 may be adjusted to vary a bend radius of housing sleeve 220. In one or more embodiments, a number of apertures in housing sleeve 220 may be adjusted to vary a radius of curvature of housing sleeve 220, e.g., when housing sleeve 220 is in a particular curved position. Illustratively, a location or a geometry of one or more apertures in housing sleeve 220 may be adjusted to vary a bend radius of housing sleeve 220. In one or more embodiments, a location or a geometry of one or more apertures in housing sleeve 220 may be adjusted to vary a radius of curvature of housing sleeve 220, e.g., when housing sleeve 220 is in a particular curved position.

In one or more embodiments, a geometry of actuation mechanism 110 may be adjusted to vary an amount of actuation of actuation control 120 configured to curve housing sleeve 220 to a particular curved position. Illustratively, a geometry of actuation mechanism guide 160 may be adjusted to vary an amount of actuation of actuation control 120 configured to curve housing sleeve 220 to a particular curved position. In one or more embodiments, a geometry of handle end cap 105 or a geometry of handle base 130 may be adjusted to vary an amount of actuation of actuation control 120 configured to curve housing sleeve 220 to a particular curved position. Illustratively, a length of shape memory wire 210 may be adjusted to vary an amount of actuation of actuation control 120 configured to curve housing sleeve 220 to a particular curved position. In one or more embodiments, a geometry of pre-formed curve 215 may be adjusted to vary an amount of actuation of actuation control 120 configured to curve housing sleeve 220 to a particular curved position. Illustratively, a location of pre-formed curve 215 relative to shape memory wire distal end 211 may be adjusted to vary an amount of actuation of actuation control 120 configured to curve housing sleeve 220 to a particular curved position.

In one or more embodiments, at least a portion of optic fiber 230 may be enclosed in an optic fiber sleeve configured to, e.g., protect optic fiber 230, vary a stiffness of optic fiber 230, vary an optical property of optic fiber 230, etc. Illustratively, optic fiber 230 may comprise a buffer, a cladding disposed in the buffer, and a core disposed in the cladding. In one or more embodiments, at least a portion of optic fiber 230 may comprise a buffer configured to protect an optical property of optic fiber 230. Illustratively, at least a portion of optic fiber 230 may comprise a buffer configured to protect an optical layer of optic fiber 230, e.g., the buffer may protect an optical layer of a curved portion of optic fiber 230. In one or more embodiments, at least a portion of optic fiber 230 may comprise a polyimide buffer configured to protect an optical property of optic fiber 230. For example, at least a portion of optic fiber 230 may comprise a Kapton buffer configured to protect an optical property of optic fiber 230.

In one or more embodiments, a steerable laser probe may comprise a pressure mechanism configured to provide a force. Illustratively, a pressure mechanism may be disposed within pressure mechanism housing 180. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 110 relative to handle proximal end 102. Illustratively, a pressure mechanism may be configured to provide a facilitating force, e.g., to facilitate a retraction of actuation mechanism 110 relative to handle proximal end 102. In one or more embodiments, a pressure mechanism may comprise a spring or a coil. Illustratively, a pressure mechanism may comprise a pneumatic system or any system configured to provide a force.

Illustratively, handle 100 may comprise one or more detents configured to temporarily house an actuation control 120. In one or more embodiments, actuation control guide 140 may comprise one or more detents configured to temporarily fix actuation control 120 in a position relative to handle proximal end 102. Illustratively, a surgeon may actuate actuation control 120 into a detent of an actuation control guide 140, e.g., to temporarily fix actuation control 120 in a position relative to handle proximal end 102. In one or more embodiments, temporarily fixing actuation control 120 in a position relative to handle proximal end 102 may be configured to temporarily fix housing sleeve 220 in a particular curved position. Illustratively, a surgeon may actuate an actuation control 120 out from a detent of an actuation control guide 140, e.g., to adjust an amount of actuation of actuation control 120 relative to handle proximal end 102. In one or more embodiments, adjusting an amount of actuation of actuation control 120 relative to handle proximal end 102 may be configured to adjust a curvature of housing sleeve 220.

Figure 4A:
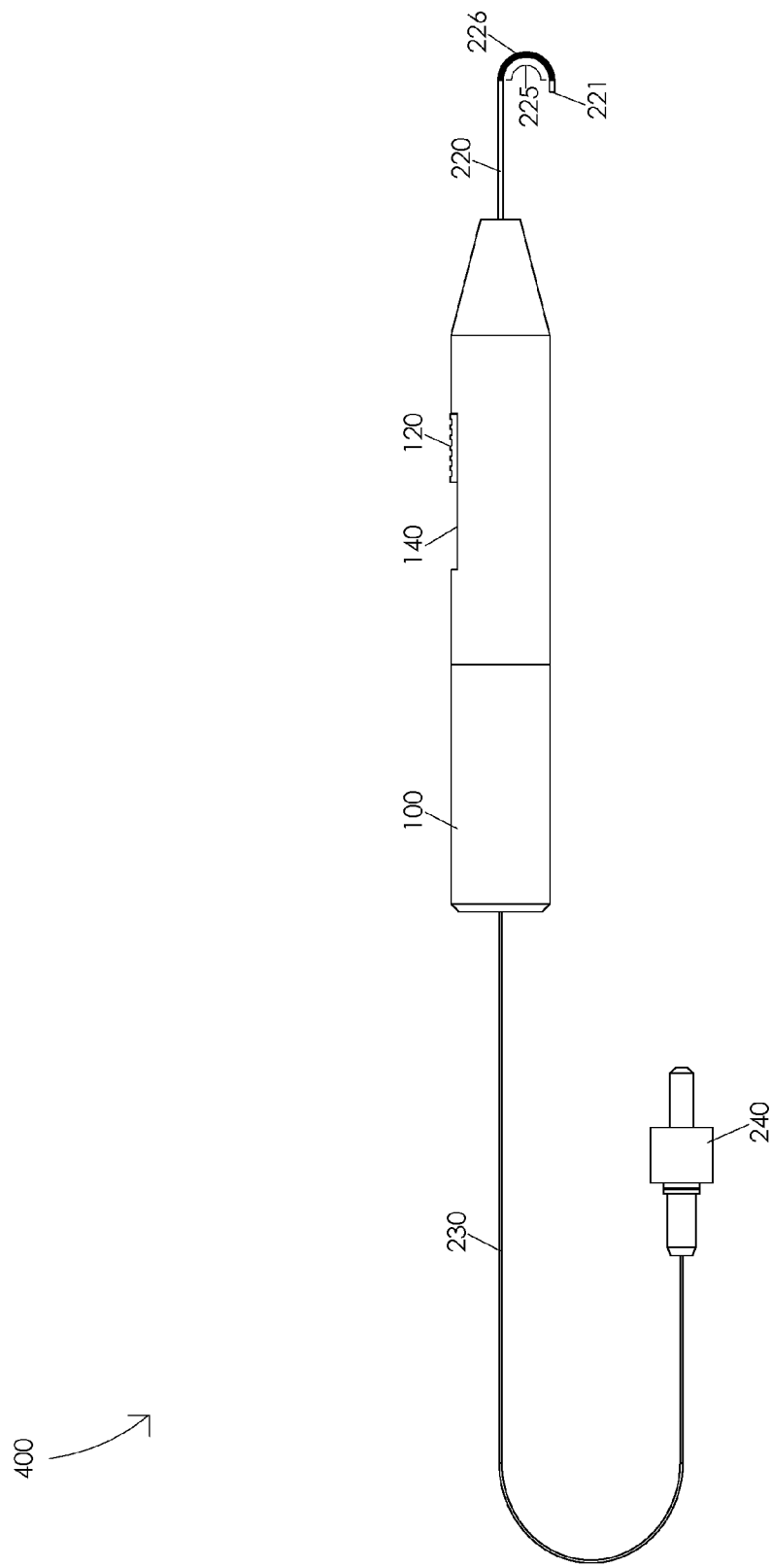
FIGS. 4A, 4B, 4C, 4D, and 4E are schematic diagrams illustrating a gradual straightening of an optic fiber.

FIGS. 4A, 4B, 4C, 4D, and 4E are schematic diagrams illustrating a gradual straightening of an optic fiber 230. FIG. 4A illustrates a fully curved optic fiber 400. In one or more embodiments, optic fiber 230 may comprise a fully curved optic fiber 400, e.g., when actuation control 120 is fully extended relative to actuation control guide proximal end 142. Illustratively, optic fiber 230 may comprise a fully curved optic fiber 400, e.g., when actuation mechanism 110 is fully extended relative to handle proximal end 102. In one or more embodiments, optic fiber 230 may comprise a fully curved optic fiber 400, e.g., when shape memory wire 210 is fully extended relative to housing sleeve 220. Illustratively, optic fiber 230 may comprise a fully curved optic fiber 400, e.g., when pre-formed curve 215 is fully extended over first housing sleeve portion 225. In one or more embodiments, a line tangent to optic fiber distal end 231 may be parallel to a line tangent to housing sleeve proximal end 222, e.g., when optic fiber 230 comprises a fully curved optic fiber 400.

Figure 4B:
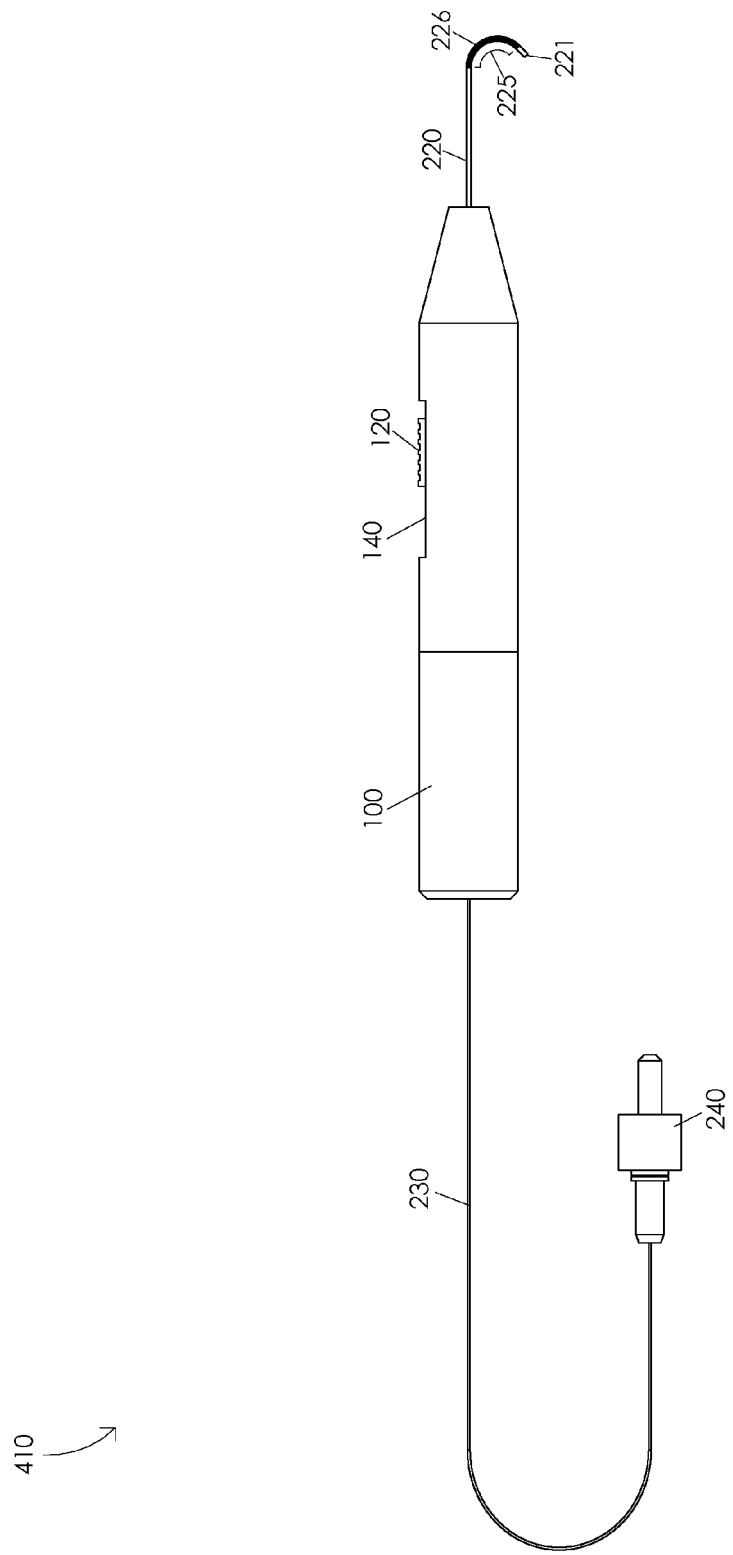

FIG. 4B illustrates an optic fiber in a first partially straightened position 410. In one or more embodiments, an actuation of actuation control 120 within actuation control guide 140, e.g., towards actuation control guide proximal end 142 and away from actuation control guide distal end 141, may be configured to gradually straighten optic fiber 230 from a fully curved optic fiber 400 to an optic fiber in a first partially straightened position 410. Illustratively, an actuation of actuation control 120 towards actuation control guide proximal end 142 and away from actuation control guide distal end 141 may be configured to retract actuation mechanism 110 within actuation mechanism guide 160, e.g., towards handle proximal end 102 and away from handle distal end 101. In one or more embodiments, a retraction of actuation mechanism 110 within actuation mechanism guide 160 may be configured to retract shape memory wire 210 relative to housing sleeve 220. Illustratively, a retraction of shape memory wire 210 relative to housing sleeve 220 may be configured to retract pre-formed curve 215 within housing sleeve 220, e.g., towards housing sleeve proximal end 222 and away from housing sleeve distal end 221. In one or more embodiments, a retraction of pre-formed curve 215 within housing sleeve 220 may be configured to retract a portion of pre-formed curve 215 away from first housing sleeve portion 225, e.g., into a portion of housing sleeve 220 configured to generally straighten pre-formed curve 215. Illustratively, a retraction of a portion of pre-formed curve 215 away from first housing sleeve portion 225, e.g., into a portion of housing sleeve 220 configured to generally straighten pre-formed curve 215, may be configured to gradually straighten housing sleeve 220. In one or more embodiments, a gradual straightening of housing sleeve 220 may be configured to gradually straighten optic fiber 230, e.g., from a fully curved optic fiber 400 to an optic fiber in a first partially straightened position 410. In one or more embodiments, a line tangent to optic fiber distal end 231 may intersect a line tangent to housing sleeve proximal end 222 at a first partially straightened angle, e.g., when optic fiber 230 comprises an optic fiber in a first partially straightened position 410. Illustratively, the first partially straightened angle may comprise any angle less than 180 degrees. For example, the first partially straightened angle may comprise a 135 degree angle.

Figure 4C:
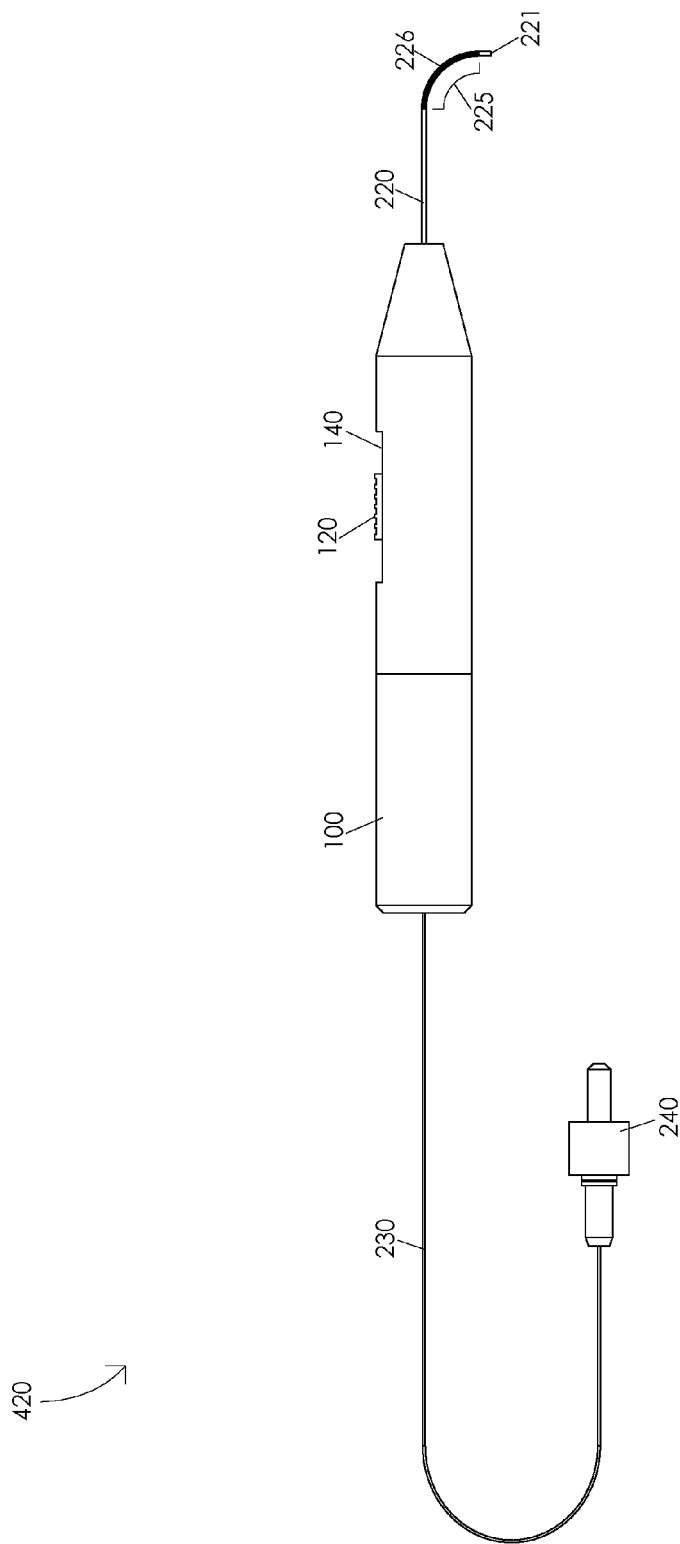

FIG. 4C illustrates an optic fiber in a second partially straightened position 420. In one or more embodiments, an actuation of actuation control 120 within actuation control guide 140, e.g., towards actuation control guide proximal end 142 and away from actuation control guide distal end 141, may be configured to gradually straighten optic fiber 230 from an optic fiber in a first partially straightened position 410 to an optic fiber in a second partially straightened position 420. Illustratively, an actuation of actuation control 120 towards actuation control guide proximal end 142 and away from actuation control guide distal end 141 may be configured to retract actuation mechanism 110 within actuation mechanism guide 160, e.g., towards handle proximal end 102 and away from handle distal end 101. In one or more embodiments, a retraction of actuation mechanism 110 within actuation mechanism guide 160 may be configured to retract shape memory wire 210 relative to housing sleeve 220. Illustratively, a retraction of shape memory wire 210 relative to housing sleeve 220 may be configured to retract pre-formed curve 215 within housing sleeve 220, e.g., towards housing sleeve proximal end 222 and away from housing sleeve distal end 221. In one or more embodiments, a retraction of pre-formed curve 215 within housing sleeve 220 may be configured to retract a portion of pre-formed curve 215 away from first housing sleeve portion 225, e.g., into a portion of housing sleeve 220 configured to generally straighten pre-formed curve 215. Illustratively, a retraction of a portion of pre-formed curve 215 away from first housing sleeve portion 225, e.g., into a portion of housing sleeve 220 configured to generally straighten pre-formed curve 215, may be configured to gradually straighten housing sleeve 220. In one or more embodiments, a gradual straightening of housing sleeve 220 may be configured to gradually straighten optic fiber 230, e.g., from an optic fiber in a first partially straightened position 410 to an optic fiber in a second partially straightened position 420. In one or more embodiments, a line tangent to optic fiber distal end 231 may intersect a line tangent to housing sleeve proximal end 222 at a second partially straightened angle, e.g., when optic fiber 230 comprises an optic fiber in a second partially straightened position 420. Illustratively, the second partially straightened angle may comprise any angle less than the first partially straightened angle. For example, the second partially straightened angle may comprise a 90 degree angle.

Figure 4D:
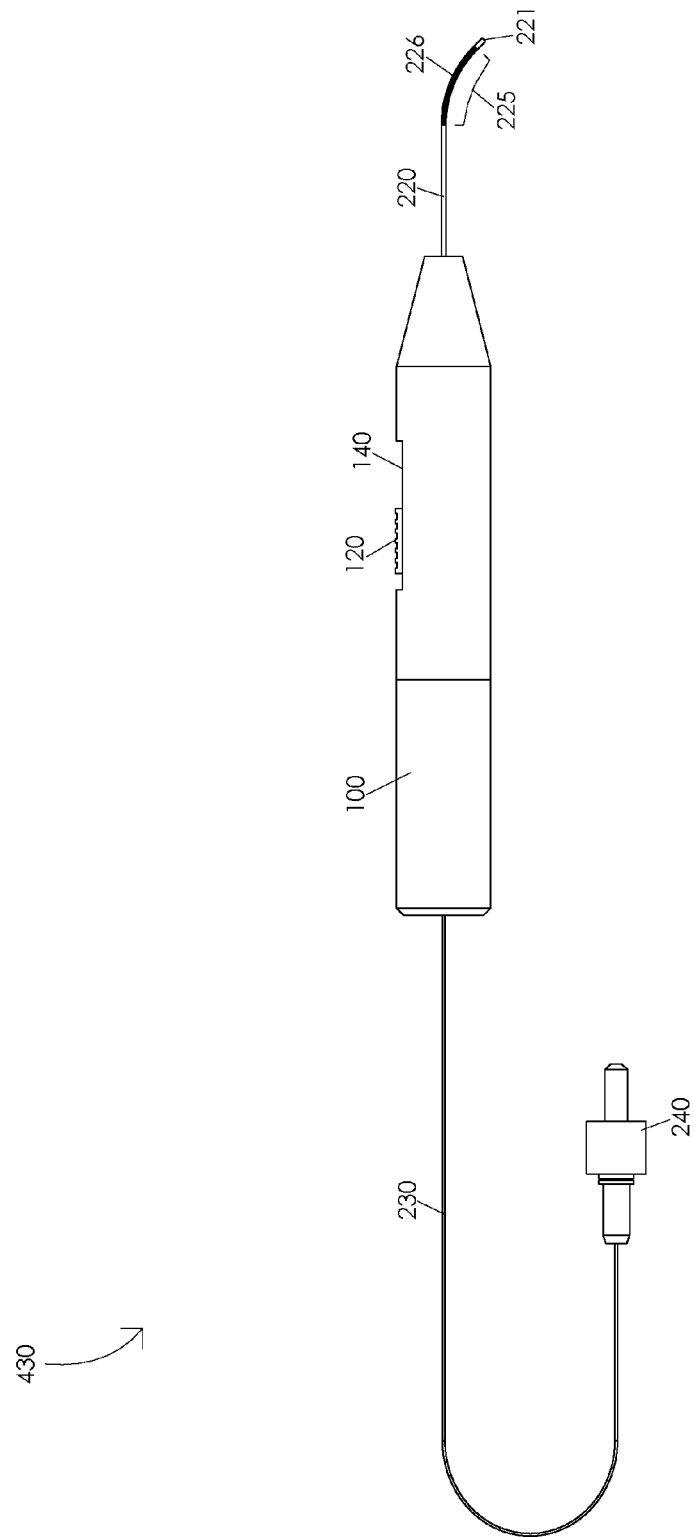

FIG. 4D illustrates an optic fiber in a third partially straightened position 430. In one or more embodiments, an actuation of actuation control 120 within actuation control guide 140, e.g., towards actuation control guide proximal end 142 and away from actuation control guide distal end 141, may be configured to gradually straighten optic fiber 230 from an optic fiber in a second partially straightened position 420 to an optic fiber in a third partially straightened position 430. Illustratively, an actuation of actuation control 120 towards actuation control guide proximal end 142 and away from actuation control guide distal end 141 may be configured to retract actuation mechanism 110 within actuation mechanism guide 160, e.g., towards handle proximal end 102 and away from handle distal end 101. In one or more embodiments, a retraction of actuation mechanism 110 within actuation mechanism guide 160 may be configured to retract shape memory wire 210 relative to housing sleeve 220. Illustratively, a retraction of shape memory wire 210 relative to housing sleeve 220 may be configured to retract pre-formed curve 215 within housing sleeve 220, e.g., towards housing sleeve proximal end 222 and away from housing sleeve distal end 221. In one or more embodiments, a retraction of pre-formed curve 215 within housing sleeve 220 may be configured to retract a portion of pre-formed curve 215 away from first housing sleeve portion 225, e.g., into a portion of housing sleeve 220 configured to generally straighten pre-formed curve 215. Illustratively, a retraction of a portion of pre-formed curve 215 away from first housing sleeve portion 225, e.g., into a portion of housing sleeve 220 configured to generally straighten pre-formed curve 215, may be configured to gradually straighten housing sleeve 220. In one or more embodiments, a gradual straightening of housing sleeve 220 may be configured to gradually straighten optic fiber 230, e.g., from an optic fiber in a second partially straightened position 420 to an optic fiber in a third partially straightened position 430. In one or more embodiments, a line tangent to optic fiber distal end 231 may intersect a line tangent to housing sleeve proximal end 222 at a third partially straightened angle, e.g., when optic fiber 230 comprises an optic fiber in a third partially straightened position 430. Illustratively, the third partially straightened angle may comprise any angle less than the second partially straightened angle. For example, the third partially straightened angle may comprise a 45 degree angle.

Figure 4E:
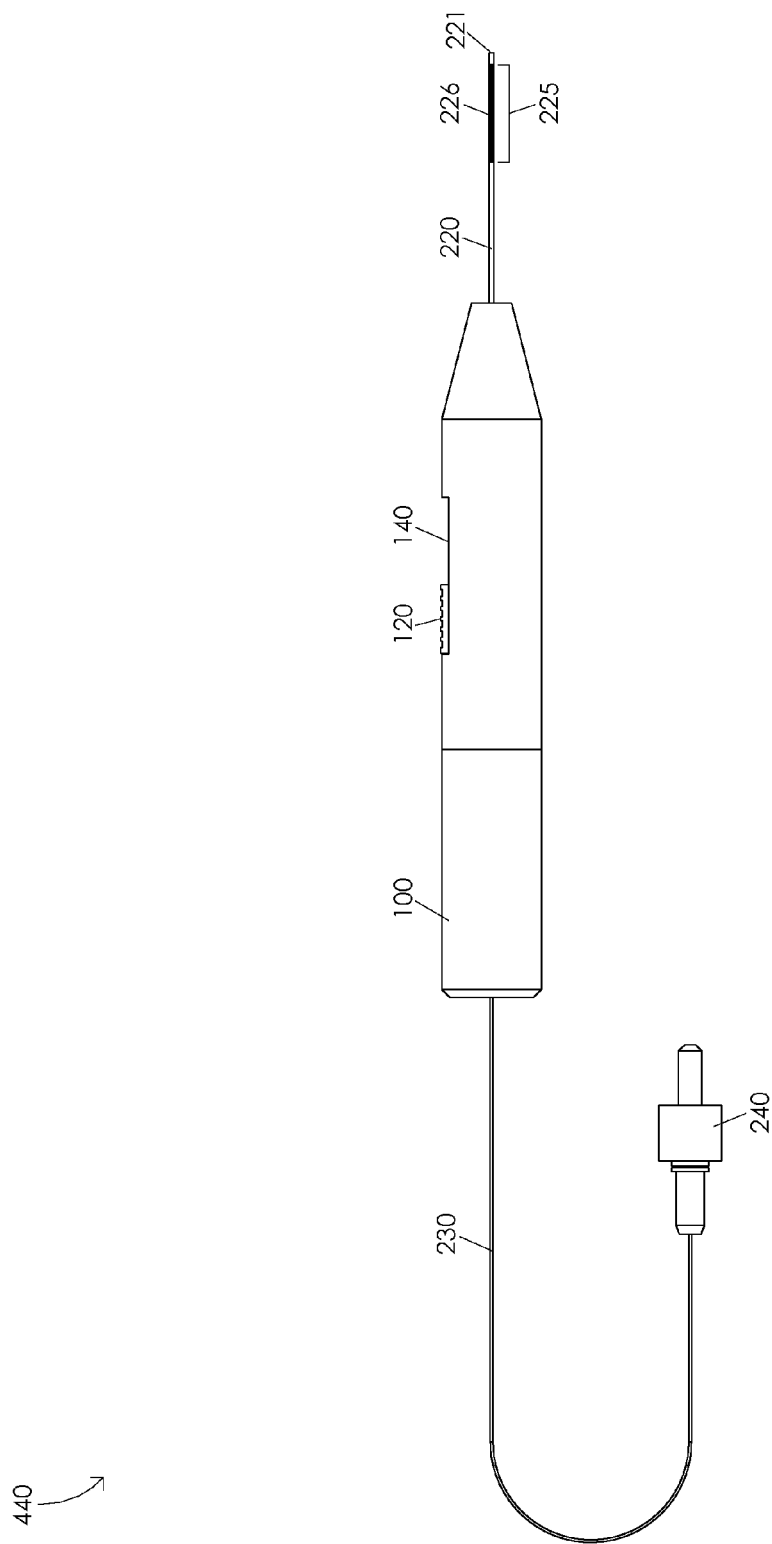

FIG. 4E illustrates an optic fiber in a fully straightened position 440. In one or more embodiments, an actuation of actuation control 120 within actuation control guide 140, e.g., towards actuation control guide proximal end 142 and away from actuation control guide distal end 141, may be configured to gradually straighten optic fiber 230 from an optic fiber in a third partially straightened position 430 to an optic fiber in a fully straightened position 440. Illustratively, an actuation of actuation control 120 towards actuation control guide proximal end 142 and away from actuation control guide distal end 141 may be configured to retract actuation mechanism 110 within actuation mechanism guide 160, e.g., towards handle proximal end 102 and away from handle distal end 101. In one or more embodiments, a retraction of actuation mechanism 110 within actuation mechanism guide 160 may be configured to retract shape memory wire 210 relative to housing sleeve 220. Illustratively, a retraction of shape memory wire 210 relative to housing sleeve 220 may be configured to retract pre-formed curve 215 within housing sleeve 220, e.g., towards housing sleeve proximal end 222 and away from housing sleeve distal end 221. In one or more embodiments, a retraction of pre-formed curve 215 within housing sleeve 220 may be configured to retract a portion of pre-formed curve 215 away from first housing sleeve portion 225, e.g., into a portion of housing sleeve 220 configured to generally straighten pre-formed curve 215. Illustratively, a retraction of a portion of pre-formed curve 215 away from first housing sleeve portion 225, e.g., into a portion of housing sleeve 220 configured to generally straighten pre-formed curve 215, may be configured to gradually straighten housing sleeve 220. In one or more embodiments, a gradual straightening of housing sleeve 220 may be configured to gradually straighten optic fiber 230, e.g., from an optic fiber in a third partially straightened position 430 to an optic fiber in a fully straightened position 440. In one or more embodiments, a line tangent to optic fiber distal end 231 may be parallel to a line tangent to housing sleeve proximal end 222, e.g., when optic fiber 230 comprises an optic fiber in a fully straightened position 440.

Illustratively, a surgeon may aim optic fiber distal end 231 at any of a plurality of targets within an eye, e.g., to perform a photocoagulation procedure, to illuminate a surgical target site, etc. In one or more embodiments, a surgeon may aim optic fiber distal end 231 at any target within a particular transverse plane of the inner eye by, e.g., rotating handle 100 to orient housing sleeve 220 in an orientation configured to cause a curvature of housing sleeve 220 within the particular transverse plane of the inner eye and varying an amount of actuation of actuation control 120. Illustratively, a surgeon may aim optic fiber distal end 231 at any target within a particular sagittal plane of the inner eye by, e.g., rotating handle 100 to orient housing sleeve 220 in an orientation configured to cause a curvature of housing sleeve 220 within the particular sagittal plane of the inner eye and varying an amount of actuation of actuation control 120. In one or more embodiments, a surgeon may aim optic fiber distal end 231 at any target within a particular frontal plane of the inner eye by, e.g., varying an amount of actuation of actuation control 120 to orient a line tangent to optic fiber distal end 231 wherein the line tangent to optic fiber distal end 231 is within the particular frontal plane of the inner eye and rotating handle 100. Illustratively, a surgeon may aim optic fiber distal end 231 at any target located outside of the particular transverse plane, the particular sagittal plane, and the particular frontal plane of the inner eye, e.g., by varying a rotational orientation of handle 100 and varying an amount of actuation of actuation control 120. In one or more embodiments, a surgeon may aim optic fiber distal end 231 at any target of a plurality of targets within an eye, e.g., without increasing a length of a portion of a steerable laser probe within the eye. Illustratively, a surgeon may aim optic fiber distal end 231 at any target of a plurality of targets within an eye, e.g., without decreasing a length of a portion of a steerable laser probe within the eye.

In one or more embodiments, one or more properties of a steerable laser probe may be adjusted to attain one or more desired steerable laser probe features. Illustratively, a relative location of pre-formed curve 215 and first housing sleeve portion 225 may be modified, e.g., optic fiber 230 may comprise a straight optic fiber 300 when shape memory wire 210 is fully extended relative to housing sleeve 220 and optic fiber 230 may comprise a fully curved optic fiber 400 when shape memory wire 210 is fully retracted relative to housing sleeve 220. For example, a portion of housing sleeve 220 located between housing sleeve distal end 221 and first housing tube portion 225 may be configured to generally straighten pre-formed curve 215.

In one or more embodiments, pre-formed curve 215 may be fully disposed in a portion of housing sleeve 220 configured to generally straighten pre-formed curve 215, e.g., when optic fiber 230 comprises a straight optic fiber 300. Illustratively, an actuation of actuation control 120 towards actuation control guide proximal end 142 and away from actuation control guide distal end 141 may be configured to retract a portion of pre-formed curve 215 over a portion of first housing sleeve portion 225, e.g., out from a portion of housing sleeve 220 configured to generally straighten pre-formed curve 215. In one or more embodiments, a retraction of a portion of pre-formed curve 215 over a portion of first housing sleeve portion 225 may be configured to gradually curve housing sleeve 220. Illustratively, a gradual curving of housing sleeve 220 may be configured to gradually curve optic fiber 230, e.g., from a straight optic fiber 300 to an optic fiber in first curved position 310.

In one or more embodiments, pre-formed curve 215 may be fully disposed over first housing sleeve portion 225, e.g., when optic fiber 230 comprises a fully curved optic fiber 400. Illustratively, an actuation of actuation control 120 towards actuation control guide distal end 141 and away from actuation control guide proximal end 142 may be configured to extend a portion of pre-formed curve 215 away from first housing sleeve portion 225, e.g., into a portion of housing sleeve 220 configured to generally straighten pre-formed curve 215. In one or more embodiments, an extension of a portion of pre-formed curve 215 into a portion of housing sleeve 220 configured to generally straighten pre-formed curve 215 may be configured to gradually straighten housing sleeve 220. Illustratively, a gradual straightening of housing sleeve 220 may be configured to gradually straighten optic fiber 230, e.g., from a fully curved optic fiber 400 to an optic fiber in a first partially straightened position 410.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. A laser probe comprising:
   an optic fiber having an optic fiber distal end and an optic fiber proximal end wherein the optic fiber is configured to transmit light;
   a housing sleeve having a housing sleeve distal end, a housing sleeve proximal end, a first housing sleeve portion, and a second housing sleeve portion wherein the first housing sleeve portion has a first stiffness and the second housing sleeve portion has a second stiffness;
   a handle having a handle distal end and a handle proximal end;
   a handle base of the handle;
   a handle end cap of the handle;
   a pressure mechanism housing of the handle;
   an optic fiber guide of the handle wherein the optic fiber guide is disposed between the pressure mechanism housing and the handle proximal end;
   an actuation mechanism guide of the handle base and the handle end cap wherein the actuation mechanism guide is disposed between the handle distal end and the handle proximal end;
   a housing sleeve housing of the handle wherein the housing sleeve housing is disposed between the handle distal end and the pressure mechanism housing and wherein the housing sleeve proximal end is disposed in the housing sleeve housing and wherein the housing sleeve proximal end is fixed in the housing sleeve housing;
   an actuation control guide having an actuation control guide distal end and an actuation control guide proximal end;
   an actuation mechanism having an actuation mechanism distal end and an actuation mechanism proximal end wherein the actuation mechanism is disposed in the actuation mechanism guide and wherein the actuation mechanism is configured to actuate within the actuation mechanism guide;
   an actuation control of the actuation mechanism wherein the actuation control is disposed in the actuation control guide between the actuation control guide distal end and the actuation control guide proximal end; and
   an inner bore of the actuation mechanism wherein the inner bore is disposed between the optic fiber guide and the pressure mechanism housing and wherein the optic fiber is disposed in the housing sleeve, the housing sleeve housing, the pressure mechanism housing, the optic fiber guide, the actuation mechanism guide, and the inner bore.

2. The laser probe of claim 1 wherein an actuation of the actuation control towards the actuation control guide distal end and away from the actuation control guide proximal end is configured to curve the optic fiber.

3. The laser probe of claim 1 wherein an actuation of the actuation control towards the actuation control guide distal end and away from the actuation control guide proximal end is configured to curve the housing sleeve.

4. The laser probe of claim 1 wherein an actuation of the actuation control towards the actuation control guide proximal end and away from the actuation control guide distal end is configured to straighten the optic fiber.

5. The laser probe of claim 1 wherein an actuation of the actuation control towards the actuation control guide proximal end and away from the actuation control guide distal end is configured to straighten the housing sleeve.

6. The laser probe of claim 1 further comprising:
   a pressure mechanism disposed in the pressure mechanism housing wherein the pressure mechanism is configured to provide a force.

7. The laser probe of claim 6 wherein an actuation of the actuation control towards the actuation control guide distal end and away from the actuation control guide proximal end is configured to curve the optic fiber.

8. The laser probe of claim 6 wherein an actuation of the actuation control towards the actuation control guide distal end and away from the actuation control guide proximal end is configured to curve the housing sleeve.

9. The laser probe of claim 6 wherein an actuation of the actuation control towards the actuation control guide proximal end and away from the actuation control guide distal end is configured to straighten the optic fiber.

10. The laser probe of claim 6 wherein an actuation of the actuation control towards the actuation control guide proximal end and away from the actuation control guide distal end is configured to straighten the housing sleeve.

11. The laser probe of claim 6 wherein the pressure mechanism is a spring.

12. The laser probe of claim 11 wherein an actuation of the actuation control towards the actuation control guide distal end and away from the actuation control guide proximal end is configured to curve the optic fiber.

13. The laser probe of claim 11 wherein an actuation of the actuation control towards the actuation control guide distal end and away from the actuation control guide proximal end is configured to curve the housing sleeve.

14. The laser probe of claim 11 wherein an actuation of the actuation control towards the actuation control guide proximal end and away from the actuation control guide distal end is configured to straighten the optic fiber.

15. The laser probe of claim 11 wherein an actuation of the actuation control towards the actuation control guide proximal end and away from the actuation control guide distal end is configured to straighten the housing sleeve.

16. The laser probe of claim 1 further comprising:
   a shape memory wire having a shape memory wire distal end, a shape memory wire proximal end, and a pre-formed curve wherein the shape memory wire is at least partially disposed in the housing sleeve.

17. The laser probe of claim 16 wherein an actuation of the actuation control towards the actuation control guide distal end and away from the actuation control guide proximal end is configured to curve the optic fiber.

18. The laser probe of claim 16 wherein an actuation of the actuation control towards the actuation control guide distal end and away from the actuation control guide proximal end is configured to curve the housing sleeve.

19. The laser probe of claim 16 wherein an actuation of the actuation control towards the actuation control guide proximal end and away from the actuation control guide distal end is configured to straighten the optic fiber.

20. The laser probe of claim 16 wherein an actuation of the actuation control towards the actuation control guide proximal end and away from the actuation control guide distal end is configured to straighten the housing sleeve.

\* \* \* \* \*